US008463382B2

(12) United States Patent
Jorgenson et al.

(10) Patent No.: US 8,463,382 B2
(45) Date of Patent: Jun. 11, 2013

(54) IMPLANTABLE LEAD FUNCTIONAL STATUS MONITOR AND METHOD

(75) Inventors: David J. Jorgenson, Bloomington, MN (US); Ross O. Starkson, Minneapolis, MN (US); Rick D. McVenes, Isanti, MN (US); Charles D. Trautmann, Ham Lake, MN (US); John D. Wahlstrand, Shoreview, MN (US); Bradley C. Peck, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 151 days.

(21) Appl. No.: 12/868,834

(22) Filed: Aug. 26, 2010

(65) Prior Publication Data
US 2010/0324629 A1    Dec. 23, 2010

Related U.S. Application Data

(63) Continuation of application No. 10/781,426, filed on Feb. 18, 2004, now Pat. No. 7,797,047, which is a continuation of application No. 10/039,667, filed on Dec. 31, 2001, now Pat. No. 6,721,600, which is a continuation-in-part of application No. 09/487,562, filed on Jan. 19, 2000, now Pat. No. 6,317,633.

(60) Provisional application No. 60/116,320, filed on Jan. 19, 1999.

(51) Int. Cl.
*A61N 1/365* (2006.01)

(52) U.S. Cl.
USPC ............................................ 607/27

(58) Field of Classification Search
USPC ............................... 607/7–8, 27–30, 5, 17, 20
See application file for complete search history.

(56) References Cited

U.S. PATENT DOCUMENTS

| 4,140,131 | A | | 2/1979 | Dutcher et al. | |
|---|---|---|---|---|---|
| 5,201,865 | A | | 4/1993 | Kuehn | |
| 5,534,018 | A | * | 7/1996 | Wahlstrand et al. | 607/27 |
| 5,713,932 | A | * | 2/1998 | Gillberg et al. | 607/27 |
| 5,741,311 | A | | 4/1998 | McVenes et al. | |
| 5,755,742 | A | * | 5/1998 | Schuelke et al. | 607/27 |
| 5,814,088 | A | | 9/1998 | Paul et al. | |
| 5,897,577 | A | | 4/1999 | Cinbis et al. | |
| 5,910,156 | A | | 6/1999 | Cinbis et al. | |
| 6,016,447 | A | * | 1/2000 | Juran et al. | 607/27 |
| 6,141,585 | A | | 10/2000 | Prutchi et al. | |
| 6,317,633 | B1 | | 11/2001 | Jorgenson et al. | |

* cited by examiner

*Primary Examiner* — Rex R Holmes
(74) *Attorney, Agent, or Firm* — Stephen W. Bauer; Michael J. Ostrom (57) ABSTRACT

A system for monitoring trends in lead impedance includes collecting data from various sources in an implantable medical device system. Lead impedance, non-physiologic sensed events percentage of time in mode switch, results of capture management operation, sensed events, adversion pace counts, refractory sense counts and similar data are used to determine the status of a lead. A set of weighted sum rules are implemented by a software system to process the data and provide displayable information to health care professionals via a programmer. The lead monitoring system includes a patient alert system for patients to seek help in the event a serious lead condition is identified.

18 Claims, 9 Drawing Sheets

| NUMBER OF COUNTER WINDOWS PER DAY | NOMINAL COUNTER WINDOW SIZE IN HOURS | TRIP POINT IF THE NUMBER OF NPS EVENTS EXCEEDS THIS COUNT. UNIPOLAR SENSING. NOMINAL/RANGE | TRIP POINT IF THE NUMBER OF NPS EVENTS EXCEEDS THIS COUNT. BIPOLAR SENSING. NOMINAL/RANGE | HOW MANY OF THESE COUNTER WINDOWS MUST HAVE NPS COUNTS ABOVE THE TRIP POINT? NOMINAL/RANGE |
|---|---|---|---|---|
| 24 | 1 hour | 2/1-32 | 1/1-32 | 16/1-24 windows |
| 12 | 2 hours | 3/1-32 | 2/1-32 | 8/1-12 windows |
| 8 | 3 hours | 4/1-32 | 3/1-32 | 5/1-8 windows |
| 6 | 4 hours | 5/1-32 | 4/1-32 | 4/1-6 windows |
| 4 | 6 hours | 8/1-32 | 6/1-32 | 3/1-4 windows |
| 3 | 8 hours | 10/1-32 | 8/1-32 | 2/1-3 windows |
| 2 | 12 hours | 14/1-32 | 12/1-32 | 1/1-2 windows |

FIG. 9b

IMPLANTABLE LEAD FUNCTIONAL STATUS MONITOR AND METHOD

RELATED APPLICATIONS

This application is a continuation of U.S. patent application Ser. No. 10/781,426, filed on Feb. 18, 2004 and now issued as U.S. Pat. No. 7,797,047, which is a continuation of U.S. patent application Ser. No. 10/039,667, filed on Dec. 31, 2001 and issued as U.S. Pat. No. 6,721,600, which is a continuation-in-part of U.S. patent application Ser. No. 09/487,562 filed on Jan. 19, 2000 and issued as U.S. Pat. No. 6,317,633, which claims the benefit of U.S. Provisional Application Ser. No. 60/116,320, filed on Jan. 19, 1999. The entire content of each of these applications is incorporated herein by reference.

FIELD OF THE INVENTION

This invention relates generally to leads used with implantable medical devices. Specifically, it relates to the monitoring of a lead's functional status, the storage of lead-related data, and an interpretation of these data into a report for use by the clinician.

BACKGROUND OF THE INVENTION

A wide assortment of automatic, body-implantable medical devices (IMDs) are presently known and commercially available. The class of such devices includes cardiac pacemakers, cardiac defibrillators and cardioverters, neural stimulators, among others. The leads used in these IMDs extend from the device through a plurality of pathways into or adjacent to various chambers of the heart, deep into the brain, into a location within the spine, and into or adjacent to other body organs, muscles and nerves, among others.

Many state-of-the-art pacemakers are capable of performing either unipolar or bipolar sensing and pacing in chambers of the heart. Unipolar pacing requires a lead with one insulated conductor and one distal pacing electrode disposed thereon. As will be appreciated by those of ordinary skill in the art, in most unipolar configurations, the casing of the implantable pulse generator (IPG) is conductive and functions as the indifferent electrode in pacing or sensing. Bipolar pacing and/or sensing, on the other hand, uses a lead with two mutually isolated conductors and two electrodes located in the heart. Typically, one electrode is disposed at the distal end of the lead and is referred to as the "tip" electrode, while the second electrode is located somewhat proximally from the tip electrode and is referred to as a "ring" electrode.

Generally, the leads are constructed of small diameter, highly flexible, reliable lead bodies made to withstand degradation by body fluids. In addition, they must be able to function in the presence of dynamic body environments that apply stress and strain to the lead body and the connections made to electrodes or sensor terminals. Some of these stresses may occur during the implantation process. Months or years later, porosity that developed from those stresses may be magnified by exposure to body fluids. These, in turn, may result in conductor or insulation related conditions that may be manifested in an intermittent or sudden Loss of Capture (LOC), out-of-range impedance and/or Loss of Sensing (LOS).

Many state-of-the-art pacemakers can be programmed to operate in either unipolar or bipolar pacing and sensing configurations using implanted leads that are responsive to changes in the patient's therapy needs. This gives the implanting physician considerable flexibility in configuring a pacing system to suit the particular needs of a patient. The state of the art in current use of leads is not completely fail safe. For example, one of the two conductors or electrodes on an implanted bipolar lead may fail for various reason, for example, a lead may fail because of breakage of a conductor due to metal fatigue, poor connection(s) between the lead(s) and the pacemaker itself, subclavian crushing of the lead, metal ion oxidation and a short circuit due to urethane/silicone breakdown. In such cases, it would be necessary to re-program the lead configuration manually or automatically to unipolar pacing and sensing in order for the pacemaker to function properly. Under current medical practice, the need for re-programming only becomes apparent upon careful examination of the patient in a clinical setting. These follow-up sessions, however, may not be conducted frequently enough to ensure proper operation of the pacemaker between such sessions.

Other problems may arise at the proximal lead end that is placed into the lead connector assembly and electrically connected via a "screw" or other connective means during implant. Due to improper connection during implant, the pacing signal may become intermittently or continuously disrupted, resulting in a high impedance or open circuit. Alternatively, the lead's distal end may become dislodged from cardiac tissue, resulting in intermittent or continuous LOC in one or both chambers. "Lead penetration" may occur during implantation when the distal end of the lead is advanced too far and protrudes through the myocardium. "Exit block", though rare, may occur due to inflammation of the cardiac tissue in contact with the distal electrode surface. The inflammation reaches such a level that either total LOC and/or LOS occurs.

When these lead problems manifest themselves, it is necessary for the clinician to diagnose the nature of the lead related condition from the available data, IMD test routines, and patient symptoms. Once diagnosed, the clinician must take corrective action, for example, re-program to unipolar polarity, open the pocket to replace the lead, reposition the electrodes or sensors, or tighten the proximal connection.

Certain IMDs, that have been clinically used or proposed, rely on lead-borne physiologic sensors that monitor physiologic conditions, for example, without limitation, blood pressure, temperature, pH, and blood gases. The operation of these sensors also depends on the integrity of the leads to which they are connected.

Lead impedance data and other parameter data, for example, without limitation, battery voltage, switching from bipolar to unipolar configuration, error counts, and LOC/LOS data, may be compiled and displayed on a programmer screen and/or printed out for analysis by the clinician. The clinician may also undertake real time IMD parameter reprogramming and testing while observing the monitored surface ECG to try to pinpoint a suspected lead related condition that is indicated by the data and/or patient and/or device symptoms.

Several approaches have been suggested to provide physicians with information and/or early detection or prevention of these lead-related conditions. Commonly assigned U.S. Pat. No. 5,861,012 (Stroebel), incorporated herein by reference, describes several approaches to automatically determine the pacing threshold. Periodically, a pacing threshold test is conducted wherein the pacing pulse width and amplitude are reduced to determine chronaxie and rheobase values to capture the heart. These threshold test data are stored in memory, and used to calculate a "safety margin" to ensure capture.

Certain external programmers that address the analysis of such data and symptoms include those disclosed in the following U.S. Pat. Nos. 4,825,869 (Sasmor et al.); 5,660,183 (Chiang et al.); and 5,891,179 (ER et al.), all incorporated herein by reference. The '869 patent describes processing a variety of uplinked, telemetered atrial and ventricular EGM data, stored parameter and event data, and the surface ECG in rule-based algorithms for determining various IPG and lead malfunctions. The '183 patent also considers patient symptoms in an interactive probability based expert system that compares data and patient systems to stored diagnostic rules, relating symptoms to etiologies so as to develop a prognosis. The '179 patent discloses a programmer that can be operated to provide a kind of time-varying display of lead impedance values in relation to upper and lower impedance limits. The lead impedance values are derived from pacing output pulse current and voltage values. These values are then either measured and stored in the IPG memory from an earlier time or represent current, real-time values that are telemetered to the programmer for processing and display.

Prior art detection of lead-related conditions and various IPG responses to such detection are set forth in the following U.S. Pat. Nos. 4,140,131 (Dutcher et al.); 4,549,548 (Wittkampf et al.); 4,606,349 (Livingston et al.); 4,899,750 (Ekwall); 5,003,975 (Hafelfinger et al.); 5,137,021 (Wayne et al.); 5,156,149 (Hudrlik); 5,184,614 (Collins); 5,201,808 (Steinhaus et al.); 5,201,865 (Kuehn); 5,224,475 (Berg et al.); 5,344,430 (Berg et al.); 5,350,410 (Kieks et al.); 5,431,692 (Hansen et al.); 5,453,468 (Williams et al.); 5,507,786 (Morgan et al.); 5,534,018 (Walhstrand et al.); 5,549,646 (Katz et al.); 5,722,997 (Nedungadi et al.); 5,741,311 (McVenes et al.); 5,755,742 (Schuelke et al.); and 5,814,088 (Paul et al.). All of these patents are incorporated herein by reference.

Most of the above-cited patents generally disclose systems for periodically measuring lead impedance and comparing the impedance measurements with upper and lower values or ranges and either storing the data for later retrieval, and/or changing a pacing or cardioversion/defibrillation path, and/or adjusting the delivered pacing energy, and/or alerting the patient by generating sound or stimulation warning signals.

The aforementioned P-8050 filed invention discloses a lead status monitor (LSM) incorporated into an IMD for processing lead-related data into a system self-test mode. The LSM provides a lead status report that identifies and declares conductor/connector issues, insulation issues, and electrode/tissue interface issues indicative of suspected lead related condition mechanisms for each lead employed in the IMD. The LSM operates employing a set of rules that process measured lead impedance values and changes in pacing pulse amplitude required to capture.

Accordingly, there is a need for a self-testing system to provide a lead status report that identifies particular lead related condition(s) for each lead employed in the IMD based on other measured values in addition to lead impedances and/or counts of various event types. What is needed is an LSM that would include measurement methods and techniques other than impedance or event counts. Such an LSM would preferably provide a rule-based algorithm for determining various lead malfunctions, a lead status report, a patient alert, and messages to clinicians to alter the IMD operating mode and/or to discontinue using a defective lead.

SUMMARY OF THE INVENTION

The present invention includes an LSM incorporated into an IMD for processing lead related data and providing a lead status report. The LSM derives its data from various sources including, for example, lead impedance, non-physiologic sensed (NPS) events, percentage of time in mode switch, results of capture management operation, sensed events, reversion pace counts, refractory sense counts. Data from these sources identifies lead conductor/connector issues, lead insulation issues, and electrode/tissue interface issues indicative of lead-related mechanisms suggestive of impending or actual lead failure for each lead employed in the IMD. The LSM employs a set of weighted sum rules used by algorithms to process data from all the above-mentioned sources to arrive at easily interpreted messages accessible to clinicians via the external programmer.

The LSM report displayed by the external programmer provides the clinician with a clear interpretation of stored lead-related data. After reading this report, the clinician is able to determine the lead status much faster than by using tests to verify lead data that have been traditionally presented by the programmer. The interpretation of the raw data along with suggestions as to further action will simplify and shorten follow-up procedures.

Optionally, the LSM may include a patient-alert capability that notifies the patient to seek assistance whenever a serious lead-related condition is identified or indicated using the LSM weighted sum rules. Additionally, the LSM includes the ability to switch the polarity configuration to one that provides an integral pathway for pacing and sensing.

Economic and operational efficiency requires that the number of periodic follow-up sessions to assess the patient's condition and the integrity of the IMD lead system be limited without comprising patient safety and care. With the assistance of the LSM and its associated messages and reports, the number of follow-up sessions may be reduced in number and/or conducted by medical personnel other than physicians thereby reducing costs. The present invention is expected to increase confidence in the self-monitoring capability of the IMD.

These and other advantages and features of the present invention will be more readily understood from the following detailed descriptions and drawings of the preferred embodiments.

DETAILED DESCRIPTION OF THE DRAWINGS

Figure 1:
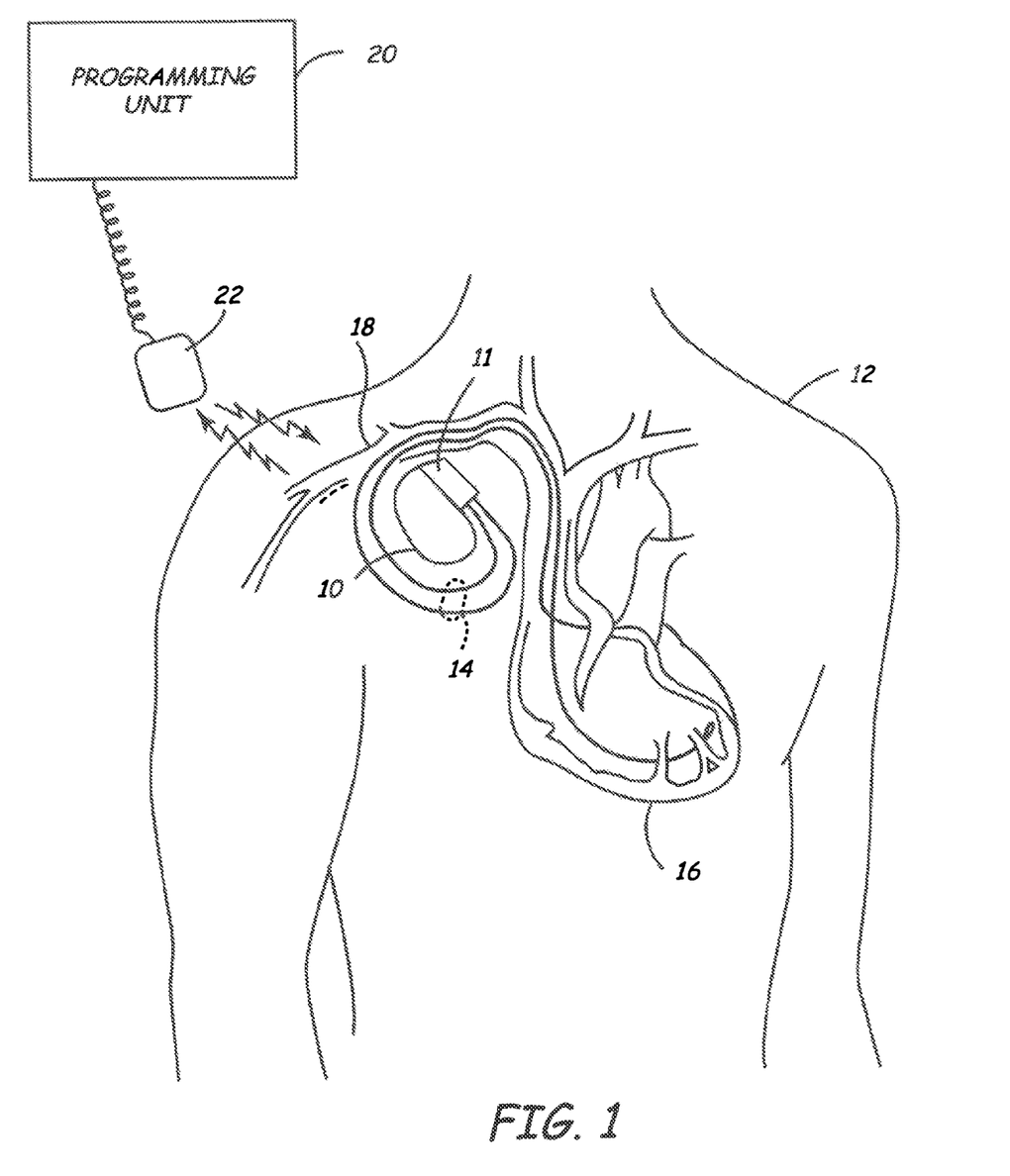
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10, for example, a pacemaker that has been implanted in patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

Although the present invention will be described herein with reference to an embodiment that includes a pacemaker, those of ordinary skill in the art having the benefit of the present disclosure will appreciate that the present invention may be advantageously practiced in connection with numerous other types of IMD systems, and indeed in any application in which it is desirable to provide a method to determine measurements and identification of other quantifiable data available from implanted lead systems.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device, generally, within 2- to 6-inches of skin contact depending on telemetry type used, such that one or more antennae within the head can send RF signals to, and receive RF signals from, an antenna disposed within the hermetic enclosure of the implanted device or disposed within the connector block of the device, in accordance with known practice in the art.

Figure 2:
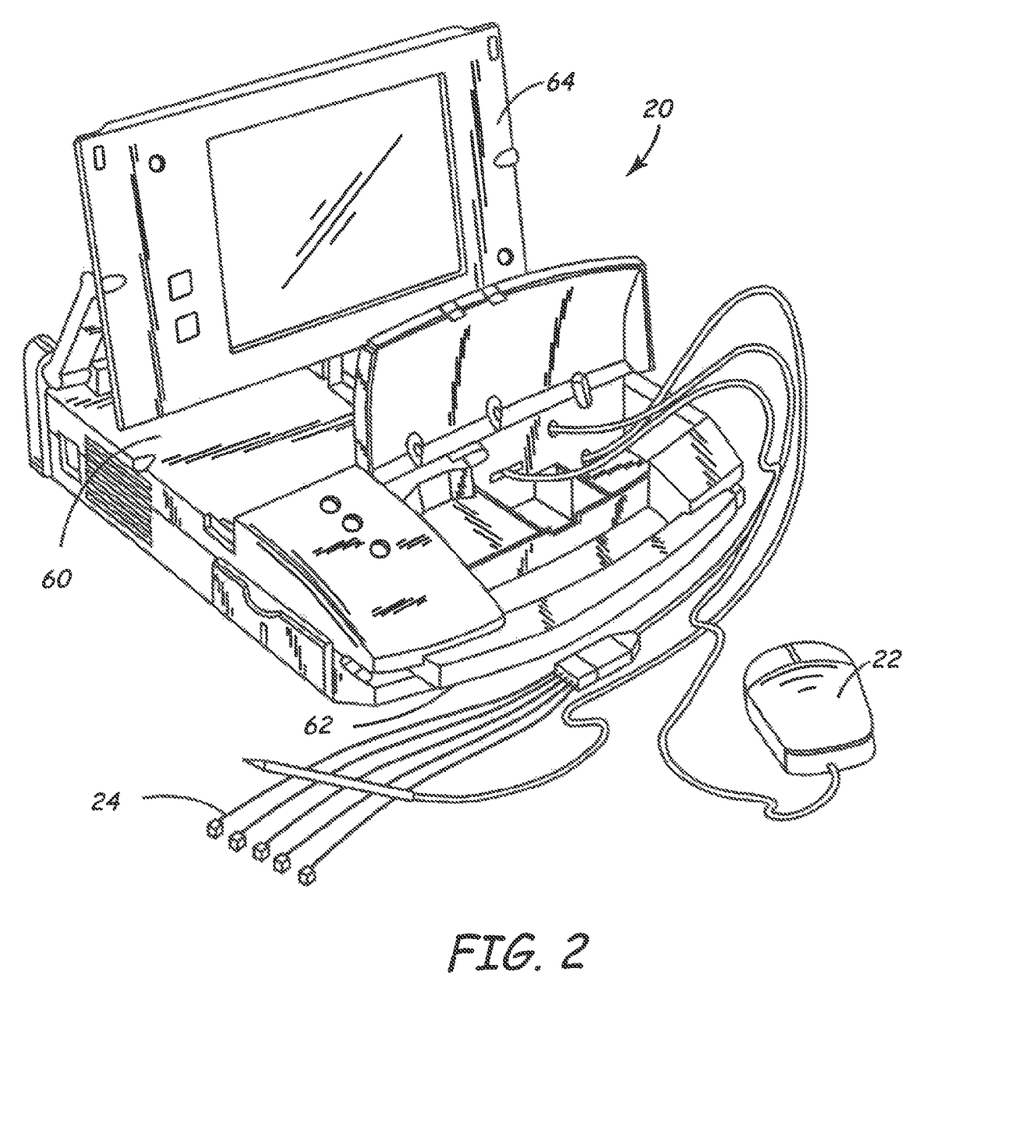
FIG. 2 is a perspective view of the external programming unit of FIG. 1.

FIG. 2 is a perspective view of programming unit 20 in accordance with the presently disclosed invention. Internally, programmer 20 includes a processing unit (not shown in this Figure) that in accordance with the present invention is a personal computer type motherboard, e.g., a computer motherboard including an Intel Pentium 3 or later microprocessor and related circuitry such as digital memory. The details of design and operation of the programmer's computer system will not be set forth in all its elements in the present disclosure, as it is believed that such details are well-known to those of ordinary skill in the art.

Referring to FIG. 2, programmer 20 comprises an outer housing 60, that is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and a hard disk drive activity indicator, (e.g., an LED, not shown) is provided to give a visible indication of hard disk activation.

As would be appreciated by those of ordinary skill in the art, it is often desirable to provide a means for determining the status of the patient's conduction system. Programmer 20 is equipped with external connectors 24 that may be used to connect to pads placed on the patient's body to detect ECG tracings from the implanted ECG leads.

In accordance with the present invention, programmer 20 is equipped with an internal printer (not shown) so that a hard copy of a patient's ECG, graphics, and reports displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer, inter alia, is the implantable device-programming unit with which the present invention may be used to determine the efficacy of the algorithms to be described below.

Figure 3:
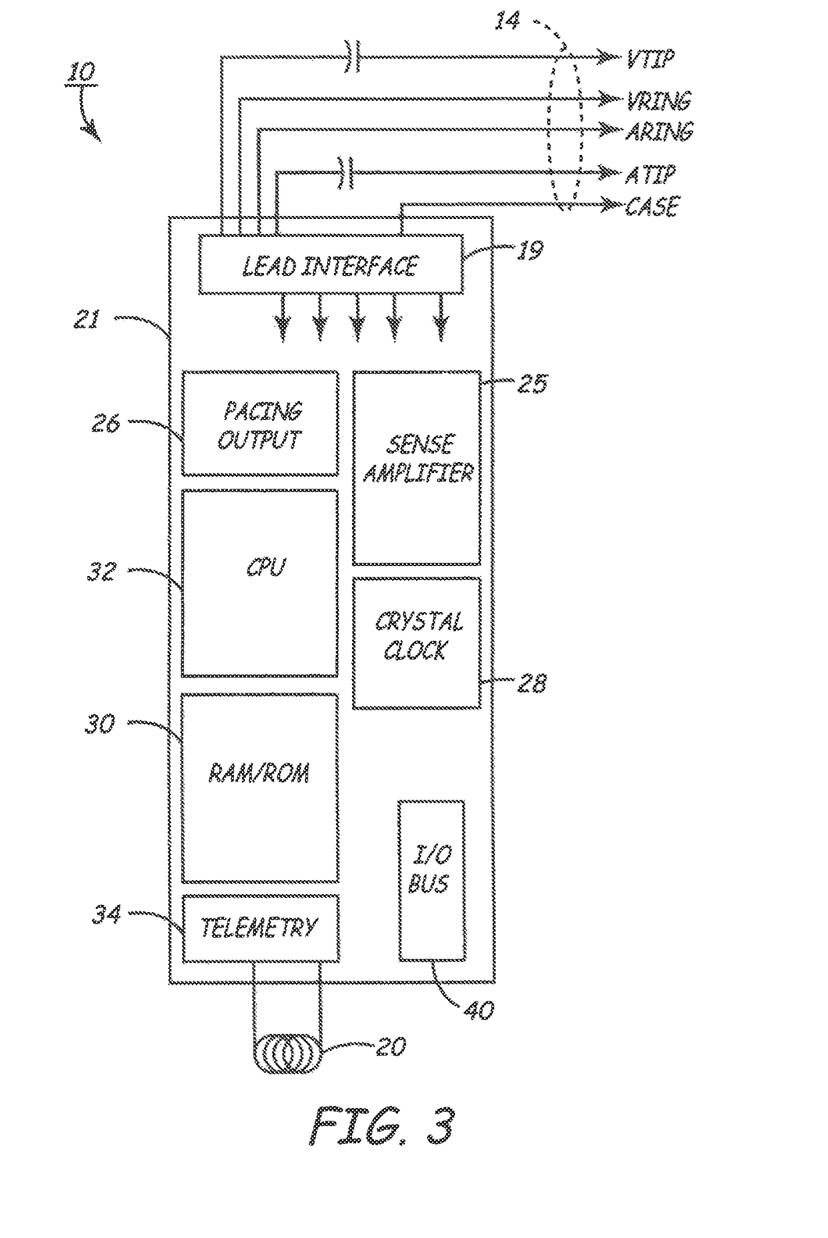
FIG. 3 is a block diagram of the implanted device from FIG. 1.

FIG. 3 is a block diagram of the electronic circuitry that typifies pulse generator 10 in accordance with the presently disclosed invention. As can be seen from FIG. 3, pacemaker 10 comprises a primary stimulation control circuit 21 for controlling the device's pacing and sensing functions. The circuitry associated with stimulation control circuit 21 may be of conventional design, in accordance, for example, with what is disclosed in U.S. Pat. No. 5,052,388 issued to Sivula et al., Method And Apparatus For Implementing Activity Sensing In A Pulse Generator. To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 3 includes sense amplifier circuitry 25, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable of communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 25 and stimulating pulse output circuit 26, in accordance with common practice, such that cardiac electrical signals may be conveyed to sensing circuitry 25, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 3, it will be apparent to those of ordinary skill in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative arrangement.

With continued reference to FIG. 3, crystal oscillator circuit 28 may be a 32,768-Hz crystal controlled oscillator that provides main timing clock signals to stimulation control circuit 21. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled Body Stimulator Output Circuit, which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 25, which is of conventional design, functions to receive electrical cardiac signals from leads 14 and to process such signals to derive event signals reflecting the occurrence of specific cardiac electrical events, including atrial depolarizations (P-waves) and ventricular depolarizations (R-waves). Sense amplifier 25 provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates to the determination of measurements of lead impedance, detection of capture and/or LOC, as well as other operations previous mentioned via algorithms that may be loaded into components described previously in FIG. 3.

Figure 4:
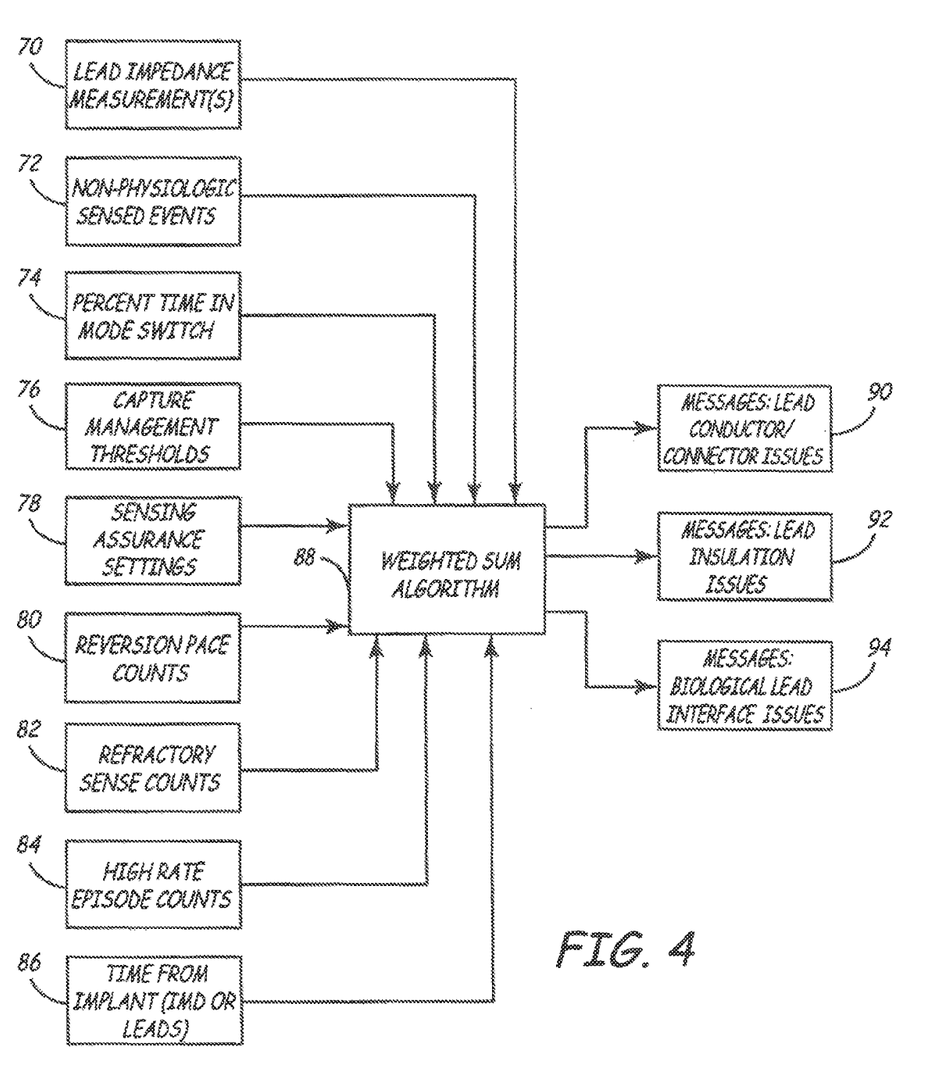
FIG. 4 is a flow diagram depicting the various factors used by the LSM algorithm and the general types of messages issued by the algorithm.

FIG. 4 is a flow diagram depicting the various data sources used by LSM algorithm 88 and the general types of messages issued by LSM algorithm 88. The LSM requires measured and other types of data to determine the status of the IMD lead(s), or lack thereof.

Lead Impedance Measurements 70 have been used for identifying problems with lead wire and/or insulation. The present invention uses a sub-threshold pacing pulse to make impedance measurements. The LSM algorithm 88 takes into account time factors, such as, for example, changes in impedance within 90 days post implant vs those that occur after 90 days post implant. Thus, lead maturation is taken into account by LSM algorithm 88. In addition, the present invention includes a method to identify the extent of the increase or decrease in impedance measurements, even though these changes may not exceed the usual limits of change, such as the nominal >4000 or <200 ohms that may be programmed to other values based on exceptional conditions or lead properties. Included also is a means to compare unipolar and bipolar impedance measurements on the same lead. LSM algorithm 88 is further discussed with reference to in FIGS. 5 and 6.

Non-Physiologic Sensed (NPS) events 72 have usually been associated with sensing of electrical noise in the unipolar configuration. If, however, the circuitry can identify when a sensed event occurs at the same time a high frequency signal occurs, generally associated with a lead wire make/break situation, these signals may be used as data to identify potential lead issues. This is particularly true if such signals are detected when the lead is in the bipolar configuration when the patient is asleep since, the assumption being while sleeping, the patient is less likely to be exposed to electrical interference. LSM algorithm 88 is further discussed with reference to FIGS. 7 and 8.

The percent of time in mode switch 74 may also be indicative of an atrial lead sensing issue. Mode switching from an atrial tracking to a non-atrial tracking mode in the presence of high atrial rates was disclosed in U.S. Pat. No. 4,363,325, issued to Roline, et al. and incorporated herein by reference in its entirety. For example, when the atrial sensed rate exceeds a programmed upper tracking rate, IPGS and PCDs operating in a dual-chamber tracking mode (DDDR or DDD) may be programmed to switch to a non-tracking mode (DDI/R, DVI/R, or VVI/R). Mode switching may occur in response to physiologic events, such as atrial flutter or fibrillation, or in response to Non-Physiologic Sensed (NPS) events, such as those due to make/break contacts that can occur due to fractured lead wire(s) or loose connectors. The present invention enables identification of a sudden increase in the percentage of time in mode switch and, at the same time, determine if this increase is due to sensing of physiologic or NPS events. Greater detail on the frequency of NPS events and how they are used by the LSM algorithm 88 is provided herein with reference to FIGS. 7 and 8.

Capture Management threshold methods 76, such as described in U.S. Pat. No. 5,861,013 issued to Peck, et al., incorporated herein by reference in its entirety, are familiar to those skilled in the art. In conjunction with such methods, the present invention establishes a reference threshold to which later capture management threshold measurements 76 can be compared. Increasing thresholds are often an indication of a lead-related condition that may relate to a failing lead. Such a reference threshold takes into account potential issues with the implanted lead(s), as well as biological/physiological issues, such as edema at the lead tissue interface, myocardial infarction, drug interactions and similar other conditions.

The reference threshold used for comparison purposes for the first 90 days post-implant period is calculated at the first pacing post-implant threshold search. Any upward threshold change exceeding a 0.25 to 1.0 V range at 1.0 ms, compared to the reference, during the first 90 day post-implant period will trigger a message per blocks 90, 92, and 94 discussed herein below. The 90-day reference threshold uses a 7-day average calculated about day 90. Any threshold change (up or down) exceeding a 0.25 to 1.75V range at 1.0 ms, compared to the reference, after the 90 day post-implant period will trigger a message per blocks 90, 92, and 94 discussed herein below.

Sensing Assurance settings 78, as disclosed in U.S. Pat. No. 6,112,119 issued to Schuelke, et al., incorporated herein by reference in its entirety, are also familiar to those skilled in the art. These methods allow the device to measure R and P-wave amplitudes and compare these to currently programmed sensitivity settings. Lead-related conditions may cause a reduction in R and P-wave amplitudes. Changes in amplitude, which are associated with changes in sensitivity settings, may then be used as indicators of impending or actual lead-related conditions.

Reversion Pace Counts 80 is a useful source of information to help identify whether an implanted lead(s) may be on the verge of failing. Typically, an implanted pacemaker will revert to an asynchronous mode (DOO, AOO, VOO) when it is in the presence of continuous electrical noise. A pacemaker, however, may not always distinguish between electrical noise and sensing of frequent make/break connections as occur when a fractured lead wire's ends tap against each other due to heart or body movements. Sensing such events may cause reversion to an asynchronous pacing mode. LSM algorithm 88, in accordance with the present invention, tracks the incidence of reversions against previously detected reference counts, and is a useful indicator of oversensing.

Refractory Sense Counts 82 may indicate any number of event types, such as the presence of high-rate atrial or ventricular events, non-physiologic sensed events, among others. When such events are detected in that portion of the refractory period occurring after an initial blanking period, they will be sensed. By comparing the number of refractory sensed events to stored EGMs from the same time period, a physician can visually determine the source of such events. In the absence of such a visual comparison that may only take place during a follow-up session, LSM algorithm 88 can identify the presence of non-physiologic sensed events 72 and compare these to signals from sensed physiologic events. Then, non-physiologic refractory sense counts 82 can compare the incidence of refractory sensed events against a reference count. If the number of refractory sense counts has increased, these data will be included in LSM weighted sum algorithm 88.

High Rate Episode Counts 84 may also be an indicator of sensing irregularities due to a failing or failed lead(s). An "episode" is used to describe a continuous high atrial or ventricular rate that extends over a period of, at least, a second or two, as opposed to discrete events. Events, constituting an episode, may be refractory or non-refractory sensed events. By tracking the number of high rate episodes from one follow-up session to another, an increase in their incidence may be used as a potential indicator of sensing irregularities. Such changes may be included in LSM weighted sum algorithm 88.

The Time from Implant 86, by default, is a 90-day timer that starts with the implant of the IMD, that is, when the lead(s) is connected to the IMD. When an IMD is "changed out," due perhaps to the need for a battery change, the IMD time from implant will be different from the lead(s) time from implant. A similar situation may occur when an atrial lead may have a different implant date than a ventricular lead. In either case, the user will have the option of selecting, via the programmer, the desired implant date that will become the new basis for LSM weighted sum algorithm 88.

Lead performance data are collected at a higher frequency during the first week post-implant, since there is a greater chance for lead-related complications during this time. These data are saved for six months. The same higher frequency of data collection automatically goes into effect whenever a sufficient number of parameters go out of range. Or, the physician can program the higher frequency of detection tool to assist in diagnosing lead-related conditions.

Weighted sum algorithm 88 uses individual weights assigned to items listed above (70 through 86). In addition, weighted sum algorithm 88 stores EGM data for physician review whenever an ambulatory or in-office lead status event (70 through 84) occurs. The algorithm sums the weights and "interprets" them for the user in the following manner:

Lead-related parameters are all within range or operating normally;

One or more of the lead parameters are out-of-range. Investigate leads.

A number of lead parameters are out-of-range and a safety problem exists. Polarity has been switched from bipolar to unipolar configuration for pacing sensing, and EGM collection.

Messages to the User 90, 92, and 94 refer to three types of lead-related conditions. Lead Conductor/Connector Messages 90 include the following:

High impedance (>4000 ohms, 2× increase over reference, among others),

Increase in threshold(s) above preset or programmed limit,

NPS counts above preset or programmed limit, and

Reduction in R and P-wave amplitude below preset or programmed limit.

Lead Insulation Messages 92 include the following:

Low impedance (<200 ohms, ½ decrease under reference, among others),

Increase in threshold(s) above preset or programmed limit,

NPS counts above preset or programmed limit, and

Reduction in R and P-wave amplitude below preset or programmed limit.

Biological Interface Messages 94 include the following:

Myocardial Penetration/Perforation

Increase in threshold(s) above preset or programmed limit, and

Reduction in R and P-wave amplitude below preset or programmed limit.

Lead Dislodgment
Increase in threshold(s) above preset or programmed limit, and
Reduction in R and P-wave amplitude below preset or programmed limit.

Exit Block
Increase in threshold(s) above preset or programmed limit, and
Possible reduction in impedance.

Figure 5:
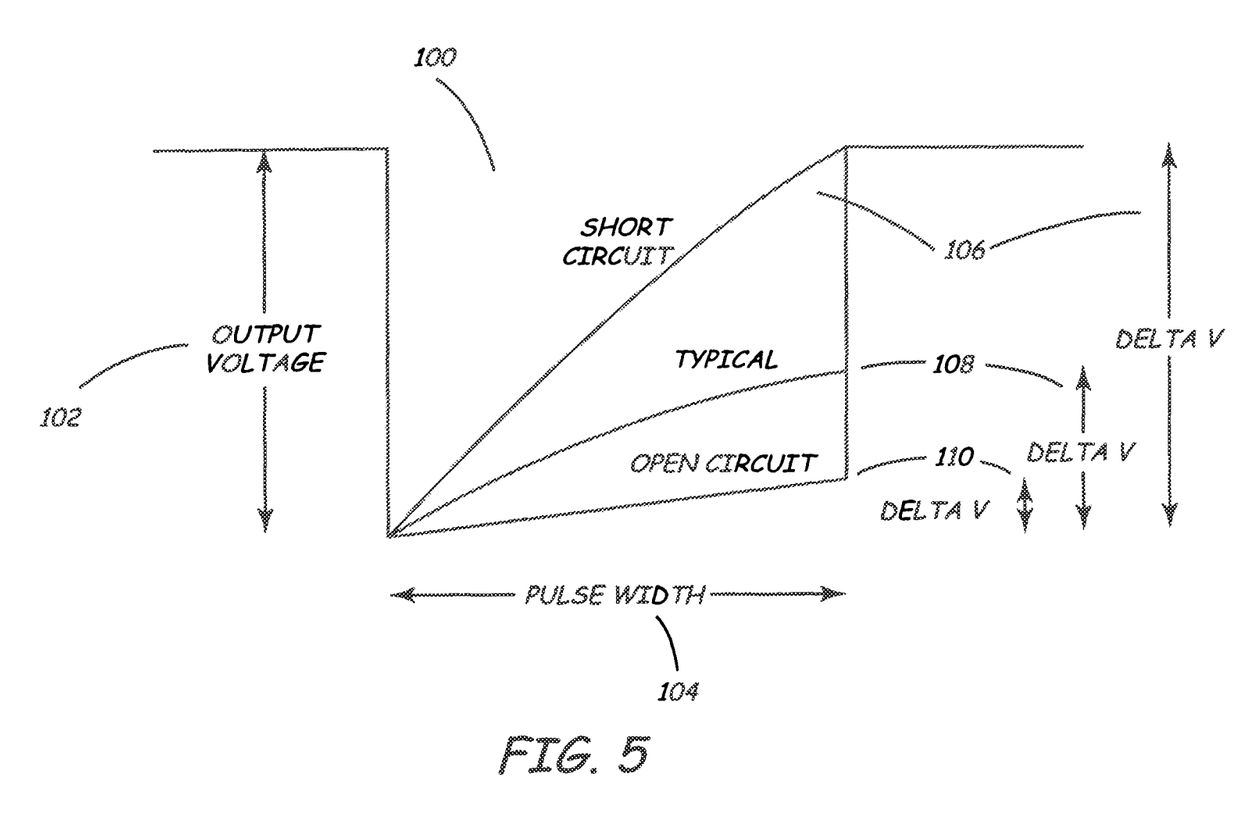
FIG. 5 is an illustration of an embodiment implemented to determine short and open circuit impedances from a typical output impedance measurement.

FIG. 5 illustrates an embodiment implemented to determine short and open circuit impedances from a typical output impedance measurement in accordance with prior art practice. The "droop" of a pacing output pulse may be used to determine varying impedances on a lead system.

Pacing pulse 100, includes programmed output voltage 102 and pulse width 104. The droop, or drop in voltage from the leading to the trailing edge of the output pulse may be used to determine the presence of a short or open circuit. Short circuit droop 106 indicates a low impedance (<200 ohms) and is a sign of a breech in the lead's insulation. Typical droop 108 is found in output pulses that range from ~500 to 4000 ohms. Open circuit droop 110 indicates a high lead impedance, >4000 ohms. High impedance loads are indicative of a break in the lead wire or an open electrical connection between the lead and IMD.

Another embodiment similar to that shown in FIG. 5 is disclosed in U.S. Pat. No. 5,741,311 issued to McVenes, et al. and incorporated herein by reference in its entirety. In the '311 patent, a short burst, 150 to 125 ms in duration with a current level of some 30 micro amps, following pacing pulses only is used to calculate lead impedances.

If these embodiments are used within the context of the present invention, the frequency of impedance measurements will vary. During the first 3 months, impedance measurements will occur at a higher frequency so as to insure detection of lead-related conditions such as perforation, dislodgment, and connector issues, among others. Any out-of-range impedance measurements due to these or other issues will be reported via the programmer upon interrogation of the IMD. Those skilled in the art would understand that a nominal range of 200 to 4000 ohms is used as a guide to judge lead integrity. These are the values that are in effect during the first 90 days. Along with minimum and maximum impedance limits, relative changes in impedance are also used as an indication of a lead-related condition.

Figure 6:
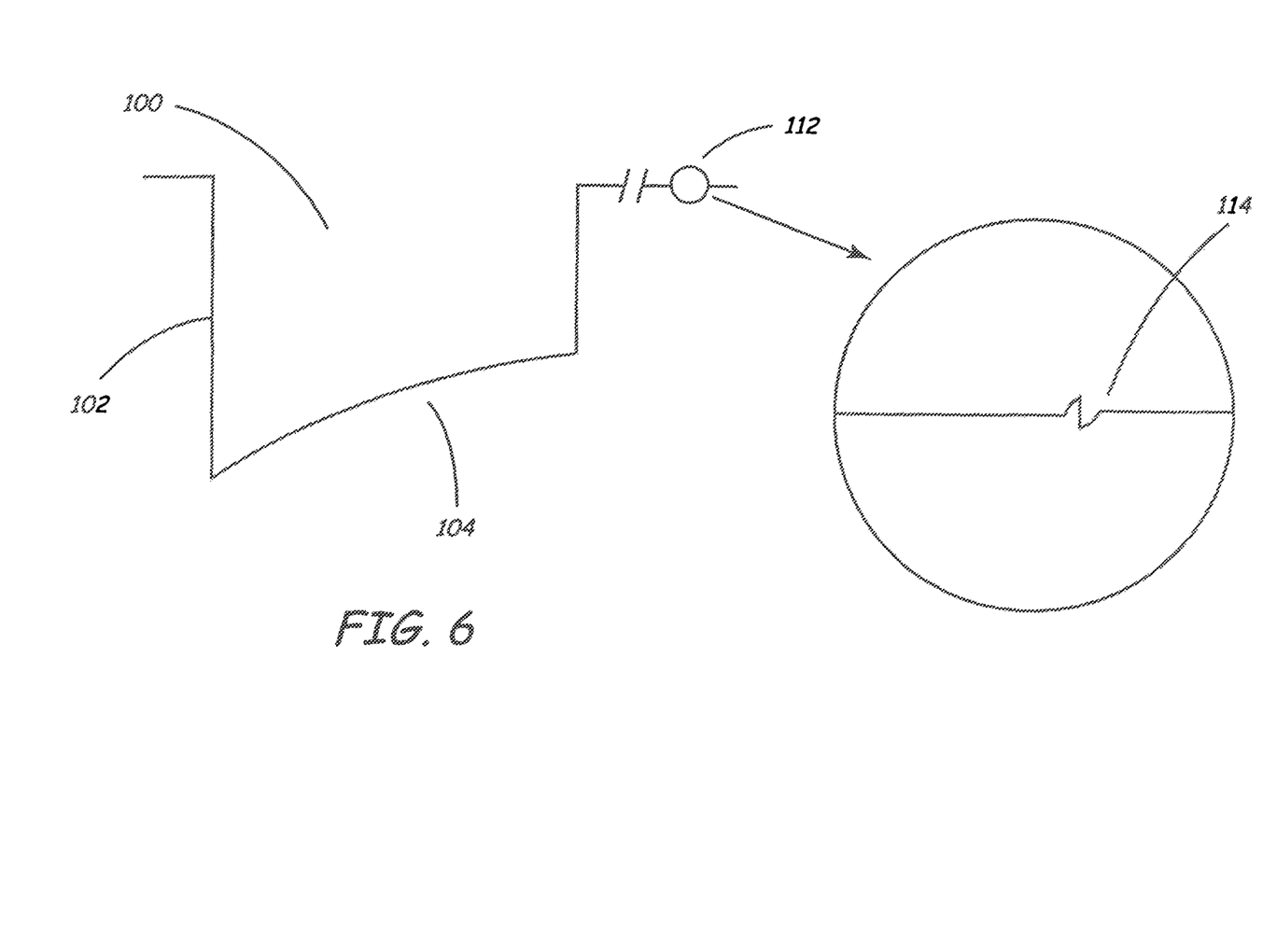
FIG. 6 is an illustration of a preferred alternative embodiment used to assess lead impedances via a subthreshold pulse.

FIG. 6 is an illustration of an alternate embodiment implemented to assess lead impedances via a subthreshold pulse. A small current is applied to the lead during the cardiac refractory period, after either a paced or spontaneous depolarization. A further requirement is that the subthreshold pulse must take place in the respective sense amplifier's blanking period. Each pathway is measured, atrial or ventricular in both configurations, unipolar and bipolar. The resulting voltage is used along with the current to calculate the impedance (R=V/I). The relative positioning 112 of subthreshold pulse 114 occurs after pacing output pulse 100. Subthreshold pulse 114 may be biphasic as shown here.

The frequency of impedance measurements will vary if the embodiment illustrated in FIG. 6 is implemented in accordance with the present invention. Particularly, during the first 3 months, impedance measurements will occur at a higher frequency so as to insure detection of lead-related complications such as perforation, dislodgment, and connector issues, among others. Any out-of-range impedance measurements due to these or other issues will be reported via the programmer upon interrogation of the IMD. The same impedance ranges disclosed in relation to FIG. 5 will also be used.

The embodiment illustrated in FIG. 6 offers several benefits. Pacing is not required, since impedance measurements can be achieved even when the patient is in his or her own intrinsic rhythm. Prior art system such as the embodiment in FIG. 5 have several drawbacks. For example, voltage output 102 and pulse width 104 as programmed may be as high as 5 V and 1 ms, or more. Some patients will feel this high voltage output. Subthreshold pulses may be used to measure both the unipolar and bipolar pathways. Paced impedances can measure only the pathway being used to pace the patient. This is especially important when the bipolar pathway is being used for sensing and the unipolar pathway is used for pacing, or vice versa.

Comparing unipolar and bipolar impedances may also lead to early detection of an insulation failure. A drop of more than 50 ohms may be detected on the bipolar pathway as compared to the unipolar. Such a difference in impedance may indicate a break in the bipolar insulation. Body fluids can then invade the bipolar coil and electrically short the lead system.

The present invention may use any of the three embodiments described above to track trends in lead impedances. Physicians have long used trend analysis techniques to assess whether or not a lead was slowly failing. In the case of trends, however, it is important to rule out "infant" failures. To ensure that the LSM is dealing with a mature lead, a lead maturation time of 90 days post lead implant was chosen. Trend analysis is used from implant to 90 days with implant values used as a reference. Trend analysis is also used from 90 days forward with reference values collected around or near 90 days post-implant. In the present invention, the LSM algorithm logs lead impedance measurements and tracks any trends. When the lead impedance is within the nominal 200 to 4000 ohm range, a 20% increase in impedance from the "stable" reference measurement will trigger a message related to lead conductor/connector issues 90. Similarly, a 50% decrease in impedance from the "stable" reference measurement will trigger a message related to lead insulation issues 92.

Figure 7A:
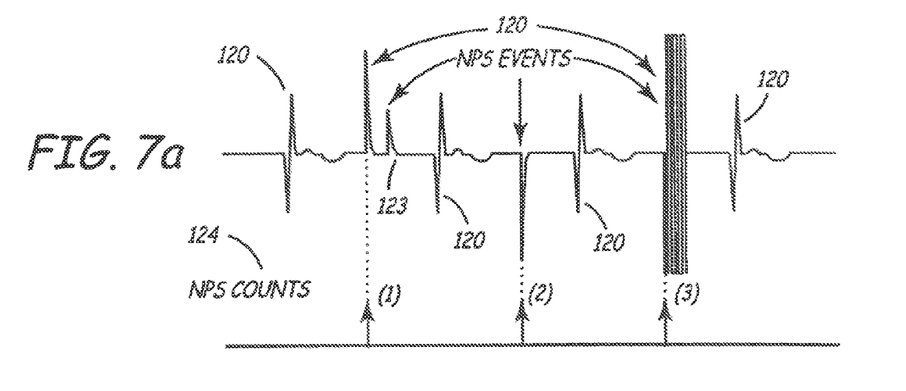
FIG. 7a, b, and c illustrate the difference between native depolarization waves and non-physiologic sensed events, and how these events can then be counted to help determine a lead-related condition.
Figure 7B:
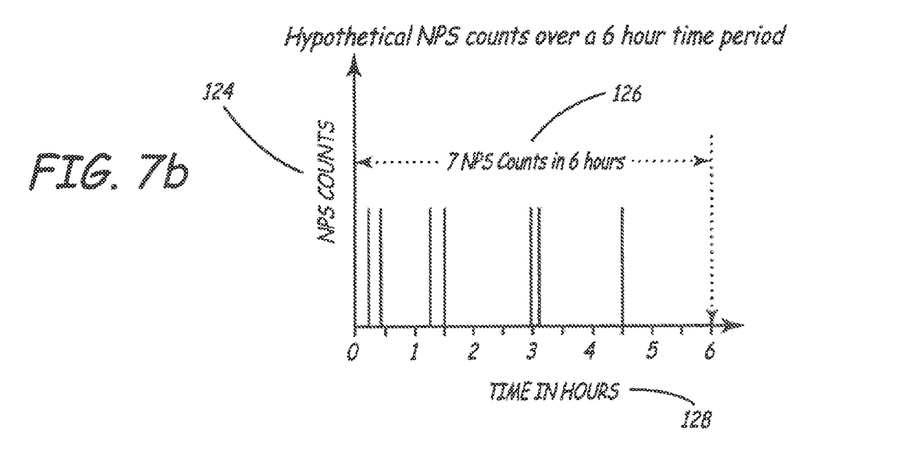
Figure 7C:
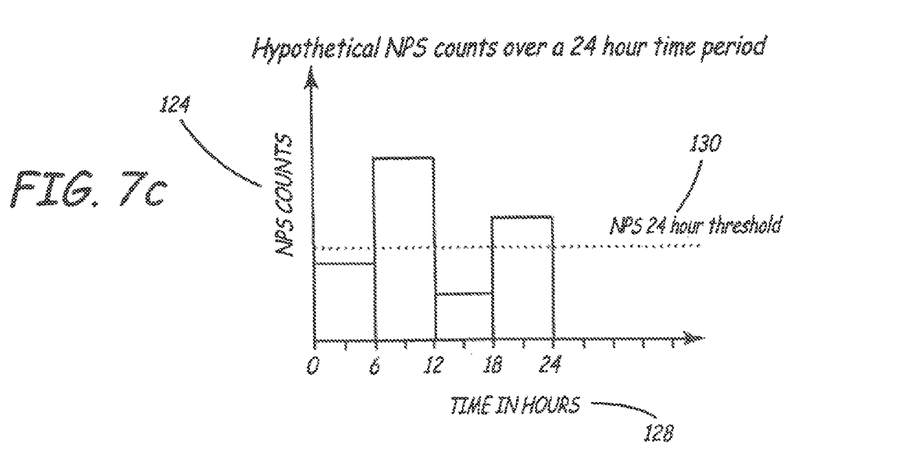

FIGS. 7a, b, and c illustrate the difference between native depolarization waves and non-physiologic sensed events, and how these events can then be counted to help determine a lead-related condition. FIG. 7a illustrates the differences between Non-Physiologic Sensed (NPS) events and intrinsic sensed events as viewed on an electrogram (EGM). Intrinsic sensed events 120 display depolarization waves that are markedly different than NPS events 122. All NPS events 122 are counted except NPS event 123, due to its proximity to the previous NPS event. NPS event 123 occurred during the blanking period following the sensing of previous NPS event 122. This conclusion is validated by the fact that NPS count 124 is not incremented at either count 1 or count 3, the latter registering only the first NPS event 122, because the remaining events are blanked.

FIG. 7b depicts hypothetical NPS counts accumulated preferably over a six-hour period 126. NPS counts 124 are broken down on the x-axis as these occur within one-hour periods 128. Further, the NPS event data from various time periods are accumulated into 24-hour period 128 as depicted in FIG. 7c. Depending on the sensitivity threshold 130 of the LSM algorithm, NPS counts may or may not qualify for consideration.

NPS events 122 may be defined as transient, high frequency signals whose characteristics may be differentiated via sense amp filters from signals generated by intrinsic depolarization waveforms 120. The close proximity of such high frequency signals 122 to intrinsic depolarization waveforms 120 may indicate the presence of a make/break situation where the conducting wire or connector has an integrity issue. NPS events 122, however, could also be due to sensing of electro-magnetic interference (EMI). EMI may have significant impact on the operation and function of unipolar pacing systems. The present invention will test for the presence of NPS events 122 in both the unipolar and bipolar configuration, which is less susceptible to external noise. Moreover, by determining if there were a number of time windows in which NPS counts 122 exceeded 24-hour threshold 130, a lead-related condition could be reasonably anticipated. Further, NPS counts 122 occurring during the patient's normal sleeping hours provide further corroboration of the possibility of a lead-related condition.

Figure 8:
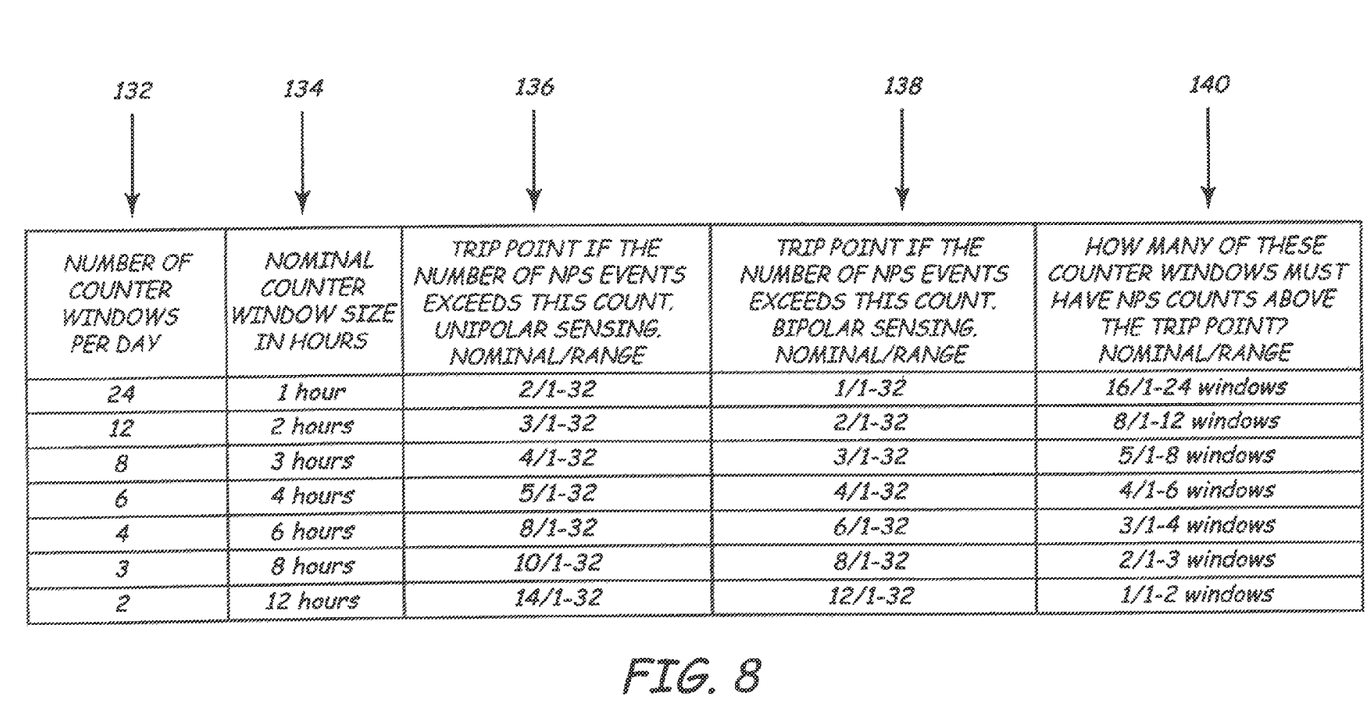
FIG. 8 is a table that relates the count of non-physiologic sensed events to the weighted sum algorithm.

FIG. 8 represents the process by which the LSM weighted sum algorithm uses the count of non-physiologic sensed events to determine the potential presence of a lead-related condition. The LSM algorithm evaluates the consistency of NPS events within the previous 24 hours. Since NPS events may be due to EMI, it is important to identify and differentiate bursts of EMI and eliminate them from consideration. To achieve this desired outcome, the LSM algorithm uses the properties shown in the table.

The number of counter windows per day 132 may be programmed from a maximum of 24 to a minimum of two per day, resulting in the window sizes of one to 12 hours 134. During each counter window, the number of NPS events must exceed the nominal or programmed number, or trip point, which differs for unipolar sensing 136 and bipolar sensing 138. Each time the NPS event counts exceed the trip point in either 136 or 138, the number of "successes" is registered in 140. For example, in row 2 with a programmed 24 windows per day, 16 of the 24 windows must have registered NPS counts above the programmed or nominal trip point. If the trip point was reached in 16 or more windows, these data are stored for further review by the clinician. If not, new measurements will overwrite the existing data.

Figure 9A:
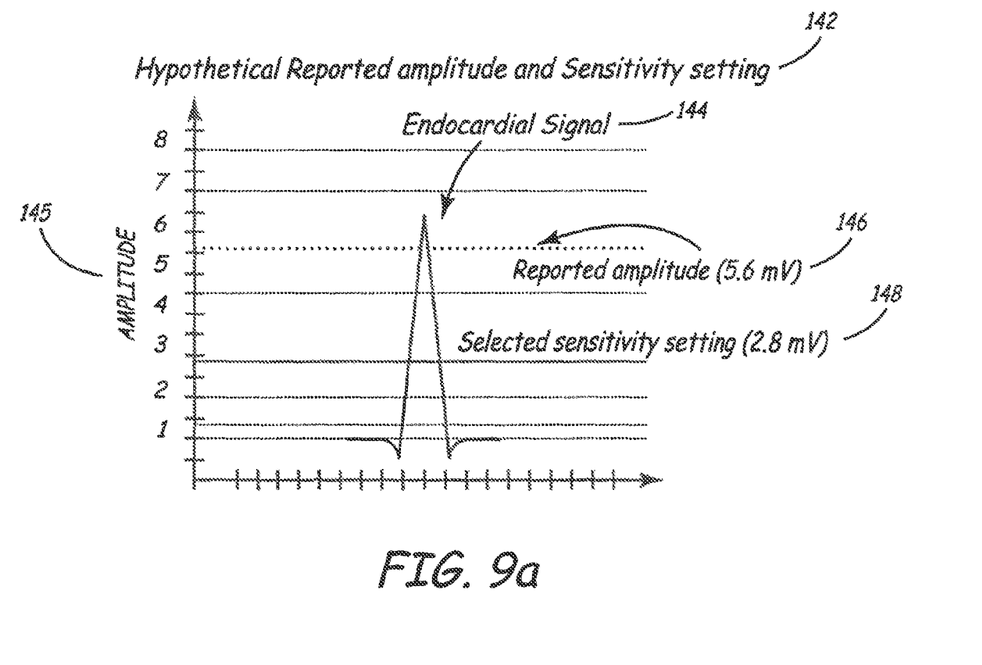
FIGS. 9a and b are illustrations depicting how the automatic sensing assurance method may help determine a lead-related condition.

FIG. 9a depicts the relationship between the amplitude of a hypothetical sensed endocardial signal and the programmed or automatically selected sensitivity settings 142. Endocardial signal 144 is sensed by the pacemaker and displayed on the programmer screen as an electrogram tracing. The pacemaker's sense amplifier related this signal to amplitude 144 and uplinks this datum as reported amplitude 146, 5.6 mV in this hypothetical example. Applying the 2:1 safety margin rule, this datum is halved resulting in selected sensitivity setting 148 or 2.8 mV in this hypothetical example.

Figure 9B:
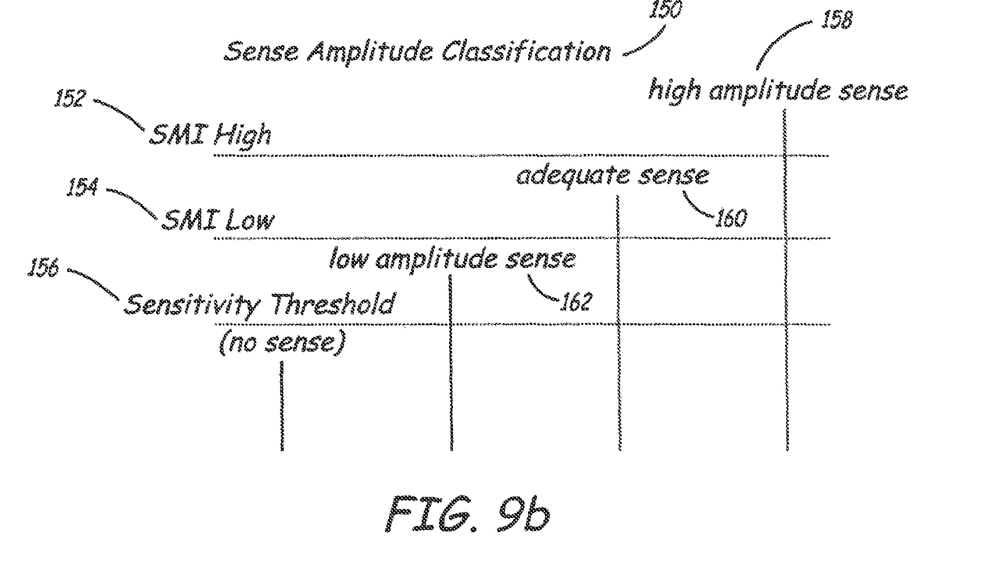

FIG. 9b illustrates the process by which the sensing assurance algorithm, implemented in the Medtronic® Kappa® 700 IPG, utilizes the data shown in FIG. 9a. The sensing assurance algorithm has sense amplitude classification 150 and evaluates all sensed events. Optimally, the amplitude of the sensed signals will be detected within Sense Margin Indicator (SMI) High 152 and SMI Low 154. When this occurs, the sensed cardiac signal is determined to be an adequate sense 160. If the amplitude of the sensed signal is above SMI high 152, it is declared to be a high amplitude sense 158 and the SMI High count is increased by unity. If or when the high counts accumulate to a certain level, sensitivity threshold 156 is increased by one setting, for example, from 2.8 to 4.0 mV. On the other hand, a low amplitude sense 162 is a sensed event that falls below SMI Low 154. Further, if or when the low counts accumulate to a certain level, sensitivity threshold 156 is decreased by one setting, for example, from 2.8 to 2.0 mV.

The Kappa 700 implementation of sensing assurance is an initial embodiment and, with finer increments in the sensitivity settings as envisioned in the present invention, may be used to establish reference P and R amplitudes. From these references, amplitude ranges may be established against which real time amplitude measurements may be compared to determine whether there is an indication of a lead-related condition.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

The invention claimed is:

1. A method comprising:
measuring, by a control circuit of an implantable medical device (IMD), a unipolar impedance value along a unipolar electrical pathway of a lead having a plurality of electrodes using one or more subthreshold pulses, wherein the lead is coupled to the IMD;
measuring, by the control circuit, a bipolar impedance value along a bipolar electrical pathway of the lead having the plurality of electrodes using one or more subthreshold pulses; and
identifying, by the control circuit, the presence of a lead-related condition based on a comparison of the unipolar impedance value measured along the unipolar electrical pathway and the bipolar impedance value measured along the bipolar electrical pathway.

2. The method of claim 1, wherein identifying, by the control circuit, the presence of the lead-related condition based on the comparison comprises identifying the presence of the lead-related when an impedance drop of more than fifty ohms is detected on the bipolar electrical pathway as compared to the unipolar electrical pathway.

3. The method of claim 2, further comprising determining that the lead-related condition is a break in the bipolar insulation when the impedance drop of more than fifty ohms is detected on the bipolar electrical pathway as compared to the unipolar electrical pathway.

4. The method of claim 1, further comprising:
sensing signals along a first sensing pathway formed by one or more of the plurality of electrodes;
sensing signals along a second sensing pathway, different from the first sensing pathway, formed by one or more of the plurality of electrodes;
wherein identifying, by the control circuit, the presence of the lead-related condition comprises identifying the presence of the lead-related condition based on the sensed signals along the first and second sensing pathways and the comparison of the unipolar impedance value measured along the unipolar electrical pathway and the bipolar impedance value measured along the bipolar electrical pathway.

5. The method of claim 4, wherein identifying, by the control circuit, the presence of the lead-related condition based on the sensed signals along the first and second sensing pathways and the comparison of the unipolar impedance value measured along the unipolar electrical pathway and the bipolar impedance value measured along the bipolar electrical pathway comprises:
determining whether a number of non-physiologic sensed events occurring along the first sensing pathway is greater than a first threshold associated with the first sensing pathway to generate a first event count;

determining whether a number of non-physiologic sensed events occurring along the second sensing pathway is greater than a second threshold associated with the second sensing pathway to generate a second event count; and identifying, by the control circuit, the presence of a lead-related condition based on the first event count and the second event count and the comparison of the unipolar impedance value measured along the unipolar electrical pathway and the bipolar impedance value measured along the bipolar electrical pathway.

6. The method of claim 5, wherein the first sensing pathway corresponds to the unipolar electrical pathway and the second sensing pathway corresponds to the bipolar electrical pathway.

7. The method of claim 5, further comprising:
determining a number of counter windows; and
determining whether a sum of the first event count and the second event count is greater than a count threshold, wherein the count threshold varies depending on the determined number of counter windows.

8. A medical device system comprising:
a lead having a plurality of electrodes; and
an implantable medical device coupled to the lead and having a control circuit that measures a unipolar impedance value along a unipolar electrical pathway using one or more subthreshold pulses, measures a bipolar impedance value along a bipolar electrical pathway using one or more subthreshold pulses, compares the unipolar impedance value measured along the unipolar electrical pathway with the bipolar impedance value measured along the bipolar electrical pathway, and identifies presence of the lead-related condition based on the comparison.

9. The system of claim 8, wherein the control circuit identifies the presence of the lead-related when an impedance drop of more than fifty ohms is detected on the bipolar electrical pathway as compared to the unipolar electrical pathway.

10. The system of claim 9, wherein the control circuit determines that the lead-related condition is a break in the bipolar insulation when the impedance drop of more than fifty ohms is detected on the bipolar electrical pathway as compared to the unipolar electrical pathway.

11. The system of claim 8, wherein the control circuit identifies the presence of the lead-related condition when an impedance drop of more than a predetermined threshold value is detected on the bipolar electrical pathway as compared to the unipolar electrical pathway.

12. The system of claim 8, wherein the control circuit:
senses signals along a first sensing pathway formed by one or more of the plurality of electrodes;
senses signals along a second sensing pathway, different from the first sensing pathway, formed by one or more of the plurality of electrodes; and
identifies the presence of the lead-related condition based on the sensed signals along the first and second sensing pathways and the comparison of the unipolar impedance value measured along the unipolar electrical pathway and the bipolar impedance value measured along the bipolar electrical pathway.

13. The system of claim 12, wherein the control circuit:
determines whether a number of non-physiologic sensed events occurring along the first sensing pathway is greater than a first threshold associated with the first sensing pathway to generate a first event count;
determines whether a number of non-physiologic sensed events occurring along the second sensing pathway is greater than a second threshold associated with the second sensing pathway to generate a second event count; and
identifies the presence of a lead-related condition based on the first event count and the second event count and the comparison of the unipolar impedance value measured along the unipolar electrical pathway and the bipolar impedance value measured along the bipolar electrical pathway.

14. The system of claim 13, wherein the first sensing pathway corresponds to the unipolar electrical pathway and the second sensing pathway corresponds to the bipolar electrical pathway.

15. The system of claim 13, wherein the control circuit:
determines a number of counter windows; and
determines whether a sum of the first event count and the second event count is greater than a count threshold, wherein the count threshold varies depending on the determined number of counter windows.

16. A medical device system comprising:
a lead having a plurality of electrodes; and
an implantable medical device coupled to lead and having a control circuit that senses signals along a first sensing pathway formed by one or more of the plurality of electrodes, senses signals along a second sensing pathway, different from the first sensing pathway, formed by one or more of the plurality of electrodes, determines whether a number of non-physiologic sensed events occurring along the first sensing pathway is greater than a first threshold associated with the first sensing pathway to generate a first event count, determines whether a number of non-physiologic sensed events occurring along the second sensing pathway is greater than a second threshold associated with the second sensing pathway to generate a second event count, and identifies the presence of a lead-related condition based on the first event count and the second event count.

17. The system of claim 16, wherein the first sensing pathway corresponds to a unipolar sensing pathway and the second sensing pathway corresponds to a bipolar sensing pathway.

18. The system of claim 16, wherein the control circuit determines a number of counter windows and identifies the presence of a lead-related condition when a sum of the first event count and the second event count is greater than a count threshold, wherein the count threshold varies depending on the determined number of counter windows.

* * * * *